United States Patent [19]

Hood, Jr.

[11] Patent Number: 4,548,088
[45] Date of Patent: Oct. 22, 1985

[54] OIL SAMPLING SYSTEM

[76] Inventor: James H. Hood, Jr., P.O. Box 10812, Knoxville, Tenn. 37919

[21] Appl. No.: 562,396

[22] Filed: Dec. 15, 1983

[51] Int. Cl.[4] ............................................. G01N 1/20
[52] U.S. Cl. ................................ 73/864.34; 137/205; 141/59; 184/1.5
[58] Field of Search ........... 73/864.34, 864.35, 864.52, 73/864.53; 137/147–149, 205; 141/27, 59, 60; 184/1.5

[56] References Cited

U.S. PATENT DOCUMENTS

| | | | |
|---|---|---|---|
| 136,264 | 2/1873 | Randall | 141/59 |
| 222,300 | 12/1879 | Neumann | 137/205 X |
| 643,605 | 2/1900 | Pendergraft | 141/59 |
| 806,095 | 12/1905 | Barrow | 141/59 |
| 892,254 | 6/1908 | Hanson | 137/205 X |
| 1,308,101 | 7/1919 | Oftedahl | 137/148 X |
| 1,572,150 | 2/1926 | Kiefer | 141/59 |
| 1,834,453 | 12/1931 | Gavaza | 137/205 X |
| 2,106,492 | 1/1938 | Adams | 141/59 |
| 2,250,517 | 7/1941 | Zolleis | 285/123 |
| 2,317,589 | 4/1943 | Collinson | 137/205 X |
| 2,405,489 | 8/1946 | Brock | 285/122 |
| 2,434,846 | 1/1948 | Hagan | 285/90 |
| 2,479,058 | 8/1949 | Botting | 285/90 |
| 2,483,740 | 10/1949 | Routen | 137/205 |
| 2,538,115 | 1/1951 | Maurer | 141/59 X |
| 3,062,056 | 11/1962 | Wicoff | 73/864.34 |
| 3,280,858 | 10/1966 | Paulson | 137/205 X |
| 3,336,061 | 8/1967 | Heisler | 287/116 |
| 3,449,958 | 6/1969 | Bailey | 73/1 G X |
| 4,378,026 | 3/1983 | Bauer | 137/205 |
| 4,450,730 | 5/1984 | Levos et al. | 73/864.35 X |
| 4,475,410 | 10/1984 | Jaeger | 73/864.34 X |

Primary Examiner—Robert Spitzer
Attorney, Agent, or Firm—Luedeka & Neely

[57] ABSTRACT

An oil sampling system for collecting an oil sample from a receptacle is disclosed. The system includes a head having a vertically disposed central bore. A collection bottle is sealingly attached to the bottom of the head in fluid communication with the central bore. A flexible tube extends from the receptacle to be sampled to the top of the head and into the central bore and is attached to the head by a coupling mechanism which selectively forms a seal between the head and the flexible tube. A vacuum mechanism in fluid communication with the central bore is used to selectively produce a partial vacuum for drawing the oil to be sampled into the flexible tube and into the collection bottle. The flexible tube extends into the interior of the collection bottle and oil to be sampled only contacts the flexible tube and the collection bottle.

14 Claims, 4 Drawing Figures

OIL SAMPLING SYSTEM

The present invention relates to oil sampling equipment and particularly relates to a manually-operated system for sampling oil from an oil receptacle.

Many industrial engines and many types of industrial mechanical equipment utilize volumes of oil in a lubrication system and often the volume of oil is quite large. For such equipment and particularly when a large volume of oil is used, it is sometimes desirable to analyze the oil rather than to routinely change it. For example, the oil may be sampled to determine whether it is maintaining its specified lubrication capabilities over time or to determine whether contaminants are present in the oil which may affect its lubrication properties or promote corrosion. In addition, analysis may detect metal particles indicating a possible wear condition in the equipment.

In order to collect samples for analysis, equipment has been developed for sampling oil, which includes a vacuum pump, a sample bottle, and a tube for insertion into the oil receptacle to be sampled. A vacuum is produced in the bottle to draw oil from the receptacle into the bottle. While known equipment is quite effective in most applications, known equipment is complicated to manufacture and is too expensive for many applications, particularly where a large number of sampling units are needed. Moreover, known equipment often does not develop sufficient vacuum to draw extremely heavy oils into the sample bottle quickly.

Therefore, a need has arisen for an oil sampling system which is simple in construction and is inexpensive to manufacture. The oil sampling system should provide an easy and inexpensive mechanism for forming and breaking a vacuum seal and should accommodate various sizes of tubing. Moreover, the oil sampling system should develop sufficient vacuum to sample extremely heavy oils.

In accordance with one form of the present invention, there is provided an oil sampling system for collecting an oil sample from a receptacle. The oil sampling system includes a head having a top and bottom. Formed in the head is a bore which extends entirely through the head from top to bottom. At the bottom of the head a collection bottle is sealingly attached in fluid communication with the bore. The system also includes a flexible tube which extends from the receptacle to be sampled to the top of the head and into the bore. A coupling mechanism is used for selectively attaching the flexible tube to the head in the bore so that a seal may be selectively formed between the head and the flexible tube. The flexible tube is maintained in fluid communication with the collection bottle when a seal is formed. The coupling mechanism also selectively releases the flexible tube to destroy the seal. A vacuum mechanism is attached to the head in fluid communication with the bore at a point between the coupling mechanism and the bottom of the head for selectively producing a partial vacuum in the bore and the collection bottle. The coupling mechanism is thus operable to release the partial vacuum in the central bore when the flexible tube is released.

In accordance with another form of the present invention, the coupling mechanism includes a coupling chamber adjacent to the central bore for receiving the flexible tube and an O-ring disposed in the chamber about the flexible tube. A compression mechanism selectively compresses the O-ring to form a seal between the interior surface of the coupling chamber and the exterior surface of the flexible tube.

In accordance with a more particular form of the present invention, the vacuum mechanism includes a vacuum bore formed in the side of the head terminating in the interior of the head, a valve wall formed in the interior of the head at the termination of the vacuum bore, and a conduit extending between the valve wall and the central bore. On the valve wall is mounted a pressure operated valve for sealingly closing the conduit when in a closed position and opening the conduit when in an open position. A vacuum cylinder is secured to the head by having a first end of the vacuum cylinder being sealingly inserted into the vacuum bore. A piston is disposed within the vacuum cylinder for reciprocating motion having a circular vacuum plate and a circular release plate maintained in a spaced-apart parallel relationship. The piston is disposed in and engages the vacuum cylinder with the vacuum plate being adjacent to the first end of the cylinder. A notch is formed at the perimeter of the release plate which extends generally radially toward the center of the release plate. A piston rod is attached to the piston and extends out of a second end of the cylinder so that the piston rod may be reciprocated manually to reciprocate the piston. An O-ring is movably fitted on the piston between the vacuum plate and the release plate for moving between a vacuum position in contact with the vacuum plate a release position in contact with the release plate. The O-ring forms a seal between the vacuum plate and the cylinder by moving into the vacuum position when the piston is moving away from the valve wall so that a partial vacuum is created in the cylinder. When the piston is moving toward the valve wall, the O-ring moves into the release position admitting fluid flow through the notch in the release plate so that the partial vacuum is released and the fluid in the cylinder goes through the notch. The pressure operated valve operates to open to the open position and to communicate the partial vacuum to the conduit and the central bore when the piston is moving away from the head, and operates to close to the closed position to maintain the partial vacuum communicated to the conduit when the piston is moving toward the valve wall. Thus, the partial vacuum in the vacuum cylinder is successively communicated to the central bore when the piston rod is reciprocated.

In accordance with a more particular form of the present invention, the coupling mechanism of the oil sampling system includes a downwardly-sloped shoulder intermediate the upper end and the lower end of the central bore and a threaded segment of the central bore adjacent to the top of the head. The coupling means further includes a coupling knob having a gripping portion configured to be turned manually and having a threaded portion engaging the threaded segment of the central bore. The threaded portion of the coupling knob terminates adjacent to a bottom surface of the coupling knob. The bottom surface of the coupling knob has a cup-shaped recess formed therein. The threaded portion of the coupling knob may be selectively drawn into or withdrawn from the central bore when the coupling knob is rotated. The coupling knob also has a bore formed through it to admit the flexible tube into the central bore. The coupling mechanism includes a coupling O-ring which is disposed between the downwardly-sloped shoulder in the central bore and the bottom surface of the coupling knob having the cup-shaped recess. The flexible tube is admitted through the coupling O-ring and is sealingly engaged by the O-ring when the coupling O-ring is engaged by and compressed between the downwardly-sloped shoulder and the bottom surface having the cup-shaped recess caused by the coupling knob being drawn into the central bore. When the coupling O-ring is compressed, the inside diameter of the coupling O-ring decreases to a contracted size to sealingly engage the flexible tube. The coupling O-ring expands when the coupling knob is withdrawn from the central bore and the inside diameter of the coupling O-ring increases to an expanded size and disengages the flexible tube. Thus, a seal is formed between the flexible tubing and the downwardly sloped shoulder when the inside diameter of the coupling O-ring is in the contracted size so that the partial vacuum in the central bore and the collection bottle is selectively communicated to the flexible tubing. Also, a fluid intake is selectively created from the exterior of the oil sampling system into the central bore when the inside diameter is in the expanded size so that the partial vacuum in the central bore and in the collection bottle is destroyed.

The present invention may best be understood by reference to the following Detailed Description when considered in conjunction with the accompanying drawings in which.

Figure 1:
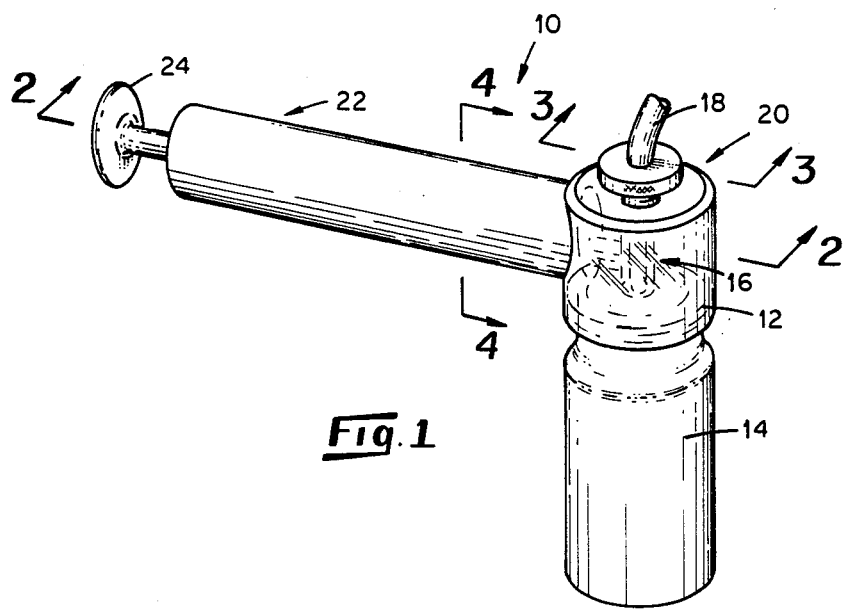
FIG. 1 is a perspective view of one form of the oil sampling system of the present invention.

Referring now to the drawings in which like reference characters designate like or corresponding parts throughout the several views, there is shown in FIG. 1 one form of an oil sampling system 10 of the present invention. The oil sampling system 10 includes a head 12 and a collection bottle 14 attached at the bottom of the head 12. As shown in broken lines in FIG. 1, a vertically disposed central bore 16 is formed in and extends through the head 12 from the top of the head 12 to the bottom of the head 12. The head 12 is cylindrical in shape and may be made of a clear plastic so that the head 12 may act as a viewing window to observe the level of oil in the sample bottle 14. A flexible tube 18 extends from the receptacle to be sampled to the top of the head 12 and into the central bore 16 and sample bottle 14. A coupling mechanism 20 is used for selectively attaching the flexible tube to the head 12 so that a seal may be selectively formed between the head 12 and the flexible tube 18 with the flexible tube 18 being in fluid communication with the collection bottle 14 and central bore 16. As also shown in FIG. 1, a vacuum mechanism 22 is attached to the head in fluid communication with the central bore 16 for selectively producing a partial vacuum in the central bore 16 and the collection bottle 14. A pull handle 24 is used to selectively operate the vacuum mechanism 22.

Figure 2:
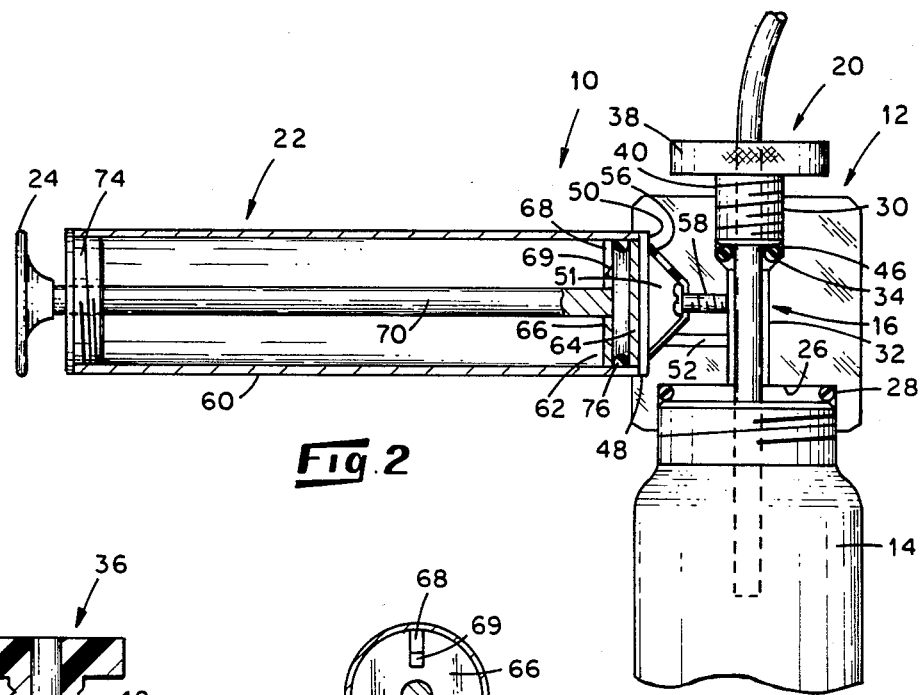
FIG. 2 is an enlarged side view of the oil sampling system of FIG. 1 shown partially in cross-section along line 2—2 of FIG. 1.

Referring now to FIG. 2 which is a side view of the oil sampling system of FIG. 1 shown partially in cross-section, the head 12 is shown to have a collection bottle recess 26 into which the collection bottle 14 is fitted. The collection bottle recess 26 and the upper portion of the collection bottle 14 are threaded so that the collection bottle 14 may be screwed into the collection bottle recess 26. A collection bottle O-ring 28 is disposed between the collection bottle and the head 12 to form a seal between the head 12 and the collection bottle 14. As previously mentioned, the central bore 16 extends from the top of the head 12 to its bottom. The central bore 16 is oriented vertically and is generally centered about the central axis of the head 12, which as noted, has a cylindrical shape. The central bore 16 has an upper area 30 and a lower area 32. The upper area 30 of the central bore 16 is enlarged. The coupling mechanism, which is designated generally by the numeral 20, is located proximate to the enlarged upper area 30 of the central bore 16 at the top of the head 12. At the transition of the enlarged upper area 30 of the central bore 16 and the lower area 32 of the central bore 16 is a downwardly-sloped shoulder 34 which is part of the coupling mechanism 20. In the enlarged upper area 30 of the central bore 16 is a threaded segment which is adjacent to the top of the head 12. A coupling knob 36 having a gripping portion 38 and a threaded portion 40 engages the threaded segment of the central bore 16. The coupling knob 36 may be rotated manually in a clockwise direction when viewed from above to selectively draw the threaded portion 40 of the coupling knob 36 into the central bore 16 or to withdraw the threaded portion 40 of the coupling knob 36 from the central bore 16 when the coupling knob 36 is rotated in a counterclockwise direction.

Figure 3:
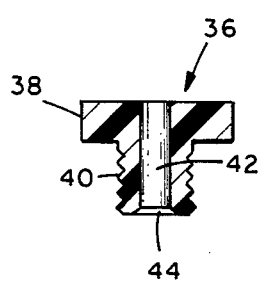
FIG. 3 is a cross-sectional view of the coupling knob of the oil sampling system of FIG. 1 taken along the line 3—3 of FIG. 1.

Referring now to FIG. 3, the coupling knob 36 is shown to have a coupling bore 42 to admit the flexible tube 18 through the coupling knob 36 and into the central bore 16. A cup-shaped recess 44 is formed into the bottom surface of the coupling knob 36. The coupling bore 42 is formed coaxially in the coupling knob 36 and is also coaxial with respect to the cup-shaped recess 44. Included in the coupling mechanism 20 as shown in FIG. 2 is a coupling O-ring 46 which is disposed between the downwardly-sloped shoulder 34 and the bottom surface of the coupling knob 36 having the cup-shaped recess 44. The coupling O-ring 46 is thus centered with respect to the central bore 16 and the coupling bore 42 and thus the flexible tube 18 is admitted through the coupling O-ring 46. The coupling knob 36, when rotated clockwise when viewed from above, causes the coupling O-ring 46 to be engaged between the downwardly-sloped shoulder 34 and the bottom surface of the coupling knob 36 having the cup-shaped recess 44. The coupling O-ring 46 is compressed when the coupling knob 36 is drawn into the central bore 16 which causes the inside diameter of the coupling O-ring 46 to decrease to a selected contracted size. A seal may selectively be formed around the flexible tube 18 by the contraction of the coupling O-ring 46. In a preferred form of the present invention, a coupling O-ring 46 having an inside diameter of five-sixteenths inch in the expanded size may be contracted to form a seal around either a three-sixteenths inch or one-fourth inch flexible tube 18. When the coupling knob 36 is withdrawn from the central bore the coupling O-ring 46 will expand to an expanded size to release the flexible tube 18 and form a fluid intake from the exterior of the system in the area between the exterior surface of the flexible tube 18 and the expanded coupling O-ring 46. FIG. 2 shows the coupling O-ring 46 in the expanded size to form the fluid intake.

Figure 4:
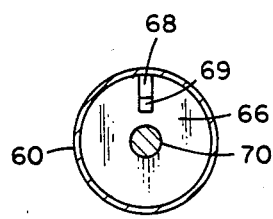
FIG. 4 is a cross-sectional view of the oil sampling system taken along line 4—4 of FIG. 1.

Referring still to FIG. 2, the vacuum mechanism 22 is shown. A vacuum bore 48 formed in the side of the head 12 terminates in the interior of the head 12. At the termination of the vacuum bore 48 in the interior of the head 12, is a valve wall 50. The valve wall 50 has a conical depression 51 extending into the head 12 which has a diameter at the base of the conical depression 51 which is nearly as large as the diameter of the valve wall 50. A conduit 52 extends between the valve wall 50 and the central bore 16. The conduit 52 is shown in FIG. 2 to be a bore located in the lower area of the head 12, but it should be understood that the conduit 52 may be located in any convenient location providing for fluid flow between the valve wall and the central bore 16. Mounted on the valve wall 50 is a pressure operated valve which is operable to sealingly close the conduit 52 when in the closed position and for opening the conduit when in the open position. In FIG. 2, the pressure operated valve is shown to include a valve flapper 56 made from oil resistant rubber or other such resilient material having sufficient size to cover the entire valve wall 50 in the area of the conical depression 51. The valve flapper 56 is configured to conform to the conical depression 51 in the valve wall 50. The valve flapper 56 is secured to the valve wall 50 by a machine screw 58 which engages a threaded bore at the apex of the conical depression 51 in the center of the valve wall 50. As shown in FIG. 2, the vacuum machanism 22 further includes a vacuum cylinder 60, the first end of which is sealingly inserted in the vacuum bore 48. The vacuum cylinder 60 is secured in the vacuum bore 48 by a friction fit, by glue or by a combination of these methods. Inside the vacuum cylinder 60 is a piston 62 which is matched with the vacuum cylinder and is dimensioned so that it may reciprocate within the vacuum cylinder 60. The piston 62 includes a circular vacuum plate 64 and a circular release plate 66 maintained in a spaced-apart parallel relationship with the piston 62 being positioned in the vacuum cylinder 60 with the vacuum plate 64 being adjacent to the first end of the vacuum cylinder 60. As is shown more clearly in FIG. 4, the release plate 66 has a notch 68 formed at the perimeter of the release plate 66 which extends generally radially toward the center of the release plate 66. The notch 68 may be formed in the release plate 66 by cutting into the release plate 66 with a circular saw or other such cutting or grinding defice. As shown in FIGS. 2 and 4, a beveled face 69 remains where the notch 68 does not pass entirely through the release plate 66.

A piston rod 70 is attached to the piston 62 and extends out of the second end of the vacuum cylinder 60 which is opposite the head 12. The piston rod 70, as noted, has a pull handle 24 which is secured onto the piston rod 70 by appropriate means. The piston rod 70 is supported at the second end of the vacuum cylinder 60 by header nut 74 which is secured to the vacuum cylinder by threads formed in the cylinder 60 and on the header nut 74 or by other such appropriate means. The header nut 74 has a bore to admit the piston rod 70 for sliding movement therein. In addition, the header nut 74 has vents (not shown) to allow the free passage of fluid in and out of the cylinder 60 through the header nut 74. The vacuum mechanism 22 further includes a piston O-ring 76 which is movably fitted on the piston 62. The piston O-ring is dimensioned to engage the inside of the cylinder 60 and is positioned between the vacuum plate 64 and the release plate 66. The piston O-ring is movable on the piston 62 between a vacuum position and a release position so that the piston O-ring 76 forms a seal between the vacuum plate 64 and the cylinder 60 by moving into the vacuum position when the piston 62 is moving away from the valve wall 50 in the head 12 causing a partial vacuum to be created in the cylinder 60. The piston O-ring 76 moves into the release position when the piston is moving toward the valve wall 50 in the head 12 so that fluid may flow through the notch 68 in the release plate and thus the partial vacuum in the cylinder is released and fluid in the cylinder 62 flows through the notch 68. The vacuum mechanism 22 is thus operable to produce a partial vacuum and to communicate the partial vacuum to the central bore 16 and the collection bottle 14. When the piston 62 is moved away from the valve wall 60 by moving the pull handle 24, a partial vacuum is created in the cylinder 60 as has been discussed. A partial vacuum acts to open the pressure operated valve 54 to the open position and the partial vacuum is communicated to the conduit 52 and thus into the central bore 12 and the collection bottle 14. When the piston 62 is moving toward the valve wall 50 or is at rest, the pressure operated valve 54 closes to the closed position to maintain the partial vacuum communicated to the conduit and causes any fluid in the cylinder 60 to flow around the vacuum plate 62 and through the notch 68 in the release plate 64. Continued reciprocation of the piston 62 causes the partial vacuum in the vacuum cylinder 62 to be successively communicated to the central bore 16 and the collection bottle 14.

In operation, the flexible tube 18 is put in contact with the oil to be sampled by inserting it through a dip stick tube or other entrance into an oil receptacle to be sampled. The other end of the flexible tube 18 is inserted through the coupling bore 42 in the coupling knob 36 and extends into the collection bottle. The coupling knob 36 is rotated in a clockwise direction until the coupling O-ring 46 forms a seal around the flexible tube 18. The pull handle 24 on the vacuum mechanism 22 is reciprocated to actuate the piston 62 in the cylinder 60. The partial vacuum created and communicated to the central bore 16 and the collection bottle 14 is further communicated to the flexible tube 18. The partial vacuum in the flexible tube 18 thus allows the oil to be sampled to flow up the flexible tube 18 and into the collection bottle 14. When sufficient oil has been collected in the collection bottle 14, the pull handle 24 is no longer reciprocated. The vacuum in the central bore 16 and the collection bottle 14 may be released by rotating the coupling knob 36 in a counterclockwise direction to cause the coupling O-ring 46 to be disengaged from the flexible tube 18. A fluid intake is created from the exterior of the sampling system 10 into the central bore and the collection bottle 14. The collection bottle 14 with a sample collected may be removed from the head 12 and a lid secured on the bottle to prevent contamination and spillage. The oil sampling system 10 may then be used to collect another sample. It may be desirable to clean or replace the flexible tube 18 before a sample is collected from another oil receptacle.

The present invention thus provides an efficient oil sampling system which is simple in operation and is inexpensive. Because the oil to be sampled only contacts the flexible tube 18 and the collection bottle 14, no cleaning need be performed between samples except for cleaning or substitution of the flexible tube 18. Since the conduit 52 is connected to the central bore 16 and not directly to the interior area of the collection bottle, contamination of the vaccum mechanism 22 is less likely. Because the coupling knob 36 is used to both secure and seal the flexible tube 18 to the head and to form a release for the vacuum in the central bore and the collection bottle, no separate release valve is necessary and the device is extremely easy to operate. The oil sampling system of the present invention provides for simplified construction since tolerances are not critical on many parts. For example, the location of central bore 16 need not be in the exact center of the head 12 and the bore which forms the conduit 52 may be formed in any convenient location. Also, the notch 68 in the release plate 66 is easily formed. The system 10 may be constructed inexpensively particularly because the cylinder 60 is secured directly to the head 12 without the need for any threaded connection. Except for the parts already discussed such as the O-rings, the flexible tube, and the head, all other parts may be constructed of any inexpensive, rigid material such as rigid plastic or a metal such as aluminum. Overall, the oil sampling system 10 provides an effective oil sampling which can collect extremely heavy oils due to the effective vacuum created by the vacuum mechanism 22. In the embodiment shown in the drawings, a vacuum as high as 25 in.Hg. (711 mm.Hg.) may be developed.

Although a particular embodiment of the present invention has been described in the foregoing detailed description, it will be understood that the invention is capable of numerous modifications without departing from the spirit of the invention.

What is claimed is:

1. An oil sampling system for collecting an oil sample from a receptacle comprising:
   a head having a top and a bottom;
   a vertically disposed central bore formed in and extending through said head from said top to said bottom;
   a collection bottle sealingly attached to said bottom of said head in fluid communication with said central bore;
   a flexible tube having an exterior surface for extending from the receptacle to be sampled to said top of said head and into said central bore;
   a coupling means for selectively attaching said flexible tube to said head in said central bore comprising seal means having an inside diameter which is selectively decreased to a contracted size to contact said exterior surface of said flexible tube to form a seal between said head and said flexible tube with said flexible tube being in fluid communication with said collection bottle and said inside diameter of said seal means being selectively increased to form a fluid intake from the exterior of the system in the area between said seal means and said exterior surface of said flexible tube and to release said flexible tube to destroy said seal;
   vacuum means attached to said head in fluid communication with said central bore for selectively producing a partial vacuum in said central bore and said collection bottle; and
   conduit means extending between said vacuum means and said bore to provide fluid communication therebetween;
   whereby, said coupling means is operable to release said partial vacuum in said central bore and said collection bottle when said inside diameter of said seal means is increased to form said fluid intake and said flexible tube is released.

2. An oil sampling system for collecting an oil sample from a receptacle comprising:
   a head having a top and a bottom;
   a vertically disposed central bore formed in and extending through said head from said top to said bottom;
   a collection bottle sealingly attached to said bottom of said head in fluid communication with said central bore;
   a flexible tube for extending from the receptacle to be sampled to said top of said head and into said central bore;
   a coupling means for selectively attaching said flexible tube to said head in said central bore so that a seal may be selectively formed between said head and said flexible tube with said flexible tube being in fluid communication with said collection bottle and for selectively releasing said flexible tube to destroy said seal, said coupling means comprising:
      a coupling chamber disposed adjacent to said bore for receiving said tube;
      an O-ring disposed in said coupling chamber about said flexible tube; and
      compression means for selectively compressing said O-ring to form a seal between the interior surface of said coupling chamber and the exterior surface of said flexible tube;
   vacuum means attached to said head in fluid communication with said central bore for selectively producing a partial vacuum in said central bore and said collection bottle;
   conduit means extending between said vacuum means and said bore to provide fluid communication therebetween; and
   said coupling means being operable to release said partial vacuum in said central bore when said flexible tube is released.

3. An oil sampling system for collecting an oil sample from an enclosed area comprising:
   a head having a top, a bottom, and at least one side;
   a vertically disposed central bore formed in and extending through said head;
   a collection bottle sealingly attached to the bottom of said head in fluid communication with said central bore;
   a flexible tube for extending from the enclosed area to be sampled to the top of said head and into said central bore;
   coupling means for attaching said flexible tube to said head in said central bore so that a seal may be selectively formed between said head and the exterior surface of said flexible tube and for selectively releasing said flexible tube to destroy said seal; and
   vacuum means comprising:
      a vacuum bore formed in the side of said head terminating in the interior of said head;
      a valve wall formed in the interior of said head at the termination of said vacuum bore;
      conduit means extending between said valve wall and said central bore;
      a pressure operated valve mounted on said valve wall for sealingly closing said conduit means when in a closed position and opening said conduit means when in an open position;
      a vacuum cylinder first and second ends, said first end being sealingly inserted into said vacuum bore;

a piston for reciprocating within said cylinder and having a circular vacuum plate and a circular release plate maintained in a spaced-apart parallel relationship, said piston being disposed in and engaging said vacuum cylinder with said vacuum plate being adjacent to said first end of said cylinder;

a notch formed at the perimeter of said release plate and extending generally radially toward the center of said release plate;

a piston rod attached to said piston and extending out of said second end of said cylinder so that said piston rod may be reciprocated manually to reciprocate said piston;

a piston O-ring dimensioned to engage said cylinder movably fitted on said piston between said vacuum plate and said release plate for moving between a vacuum position in contact with vacuum plate and release position in contact with said release plate, said O-ring forming a seal between said vacuum plate and said cylinder when said piston is moving away from said valve wall in said head so that a partial vacuum is created in said cylinder and for admitting fluid flow through said notch in said release plate by moving into said release position when said piston is moving toward said valve wall so that said partial vacuum is released and fluid in said cylinder flows through said notch; and said pressure operated valve operating to operate said open position and to communicate said vacuum to said conduit means and said central bore when said piston is moving away from said valve wall, and operating to close to said closed position to maintain said partial vacuum communicated to said conduit means when said piston is moving toward said valve wall, whereby said partial vacuum in said vacuum cylinder is successively communicated to said central bore when said piston rod is reciprocated.

4. The oil sampling system of claim 3 wherein said valve wall has a conical depression formed therein.

5. The oil sampling system of claim 4 wherein said pressure-operated valve comprises:
a resilient valve flapper disposed in said conical depression for covering said conduit means when said valve is in the closed position; and
means for securing said resilient valve flapper to said valve wall at the apex of said conical depression.

6. The oil sampling system of claim 5 wherein said means for securing said resilient valve flapper comprises:
a threaded bore formed in and extending into said valve wall at the apex of said conical depression; and
a machine screw for engaging said threaded bore.

7. The oil sampling system for claim 3 wherein said first end of said vacuum cylinder is secured in said vacuum bore by friction fit.

8. The oil sampling system of claim 3 further comprising glue to secure said first end of said vacuum cylinder inserted into said vacuum bore.

9. The oil sampling system of claim 3 wherein said head is made of clear plastic.

10. An oil sampling system for collecting an oil sample from an enclosed area comprising:
a head having a top and bottom;
a vertically disposed central bore formed in and extending through said head, said bore having an upper end and a lower end;
a collection bottle sealingly attached to said bottom of said head in fluid communication with said central bore;
a flexible tube for extending from the enclosed area to be sampled to said top of said head and into said central bore;
vacuum means attached to said head in fluid communication with said bore for selectively producing a partial vacuum in said central bore and said collection bottle; and
coupling means for sealingly attaching said flexible tube to said head in said central bore and releasing said flexible tube, said coupling means comprising:
a downwardly-sloped shoulder intermediate said upper end and said lower end of said central bore;
a threaded segment of said central bore adjacent to said top of said head;
a coupling knob having a gripping portion configured to be turned manually and having a threaded portion engaging said threaded segment of said central bore, said threaded portion terminating adjacent to a bottom surface of said coupling knob having a cup-shaped recess formed therein, said threaded portion of said coupling knob being selectively drawn into or withdrawn from said central bore when said coupling knob is rotated;
a coupling bore formed in said coupling knob to admit said flexible tube through said coupling knob and into said central bore; and
a coupling O-ring having an inside diameter being disposed between said downwardly-sloped shoulder in said central bore and said bottom surface having said cup-shaped recess and to admit said flexible tube therethrough, said coupling O-ring being engaged by and being compressed between said downwardly-sloped shoulder and said bottom surface having said cup-shaped recess when said threaded portion of said coupling knob is drawn into said central bore causing said inside diameter of said coupling O-ring to decrease to a contracted size and sealingly engage said flexible tube, said coupling O-ring expanding when said threaded portion of said coupling knob is withdrawn from said central bore causing said inside diameter of said coupling O-ring to increase to an expanded size and disengage said flexible tube, whereby, a seal is formed between said flexible tubing and said downwardly-sloped shoulder when said inside diameter is in the contracted size so that said partial vacuum in said central bore and said collection bottle is selectively communicated to said flexible tubing, and whereby a fluid intake is created from the exterior of the oil sampling system into said central bore when said inside diameter is in the expanded size so that said partial vacuum in said central central bore and said collection bottle is destroyed.

11. The oil sampling system of claim 10 wherein said head is made of clear plastic.

12. The oil sampling system of claim 10 wherein said inside diameter of said O-ring is decreased to a contracted size ranging from one-quarter inch to three-sixteenths inch.

13. The oil sampling system of claim 10 wherein said gripping portion of said coupling knob is a disc having a knurled edge.

14. The oil sampling system of claim 10 wherein said vacuum means comprises:
- a vacuum bore formed in the side of said head terminating in the interior of said head;
- a valve wall formed in the interior of said head at the termination of said vacuum bore;
- conduit means extending between said valve wall and said central bore;
- a pressure operated valve mounted on said valve wall for sealingly closing said conduit means when in a closed position and opening said conduit means when in an open position;
- a vacuum cylinder having first and second ends, said first end being sealingly inserted into said vacuum bore;
- a piston for reciprocating within said cylinder and having a circular vacuum plate and a circular release plate maintained in a spaced-apart parallel relationship, said piston being disposed in and engaging said vacuum cylinder with said vacuum plate being adjacent to said first end of said cylinder;
- a notch formed at the perimeter of said release plate and extending generally radially toward the center of said release plate;
- a piston rod attached to said piston and extending out of said second end of said cylinder so that said piston rod may be reciprocated manually to reciprocate said piston;
- a piston O-ring dimensioned to engage said cylinder movably fitted on said piston between said vacuum plate and said release plate for moving between a vacuum position in contact with vacuum plate and release position in contact with said release plate, said O-ring forming a seal between said vacuum plate and said cylinder by moving into said vacuum position when said piston is moving away from said valve wall in said head so that a partial vacuum is created in said cylinder and for admitting fluid flow through said notch in said release plate by moving into said release position when said piston is moving toward said valve wall so that said partial vacuum is released and fluid in said cylinder flows through said notch; and
- said pressure operated valve operating to open to said open position and to communicate said partial vacuum to said conduit means and said central bore when said piston is moving away from said valve wall, and operating to close to said closed position to maintain said partial vacuum communicated to said conduit means when said piston is moving toward said valve wall, whereby said partial vacuum in said vacuum cylinder is successively communicated to said central bore when said piston rod is reciprocated.

* * * * *